United States Patent
Kobayashi et al.

(10) Patent No.: US 7,291,685 B2
(45) Date of Patent: Nov. 6, 2007

(54) PROCESS FOR PRODUCING LOW POLYMER OF α-OLEFIN

(75) Inventors: Ryoichi Kobayashi, Chiba (JP); Shigeki Kura, Chiba (JP)

(73) Assignee: Idemitsu Kosan Co. Ltd., Tokyo (JP)

( * ) Notice: Subject to any disclaimer, the term of this patent is extended or adjusted under 35 U.S.C. 154(b) by 29 days.

(21) Appl. No.: 10/489,611

(22) PCT Filed: Sep. 19, 2002

(86) PCT No.: PCT/JP02/09619

§ 371 (c)(1),
(2), (4) Date: Sep. 27, 2004

(87) PCT Pub. No.: WO03/029170

PCT Pub. Date: Apr. 10, 2003

(65) Prior Publication Data

US 2005/0020866 A1  Jan. 27, 2005

(30) Foreign Application Priority Data

Sep. 27, 2001  (JP)  ............ 2001-295408

(51) Int. Cl.
*C08F 2/00* (2006.01)
*C07C 2/04* (2006.01)

(52) U.S. Cl. .............. 526/81; 526/74; 585/950; 585/921; 585/922; 585/901; 585/504

(58) Field of Classification Search .......... 526/71, 526/74, 81, 67, 160; 502/9; 585/291, 921, 585/504; 134/21, 22

See application file for complete search history.

(56) References Cited

U.S. PATENT DOCUMENTS 3,352,840 A  11/1967  Oktay et al. ............ 260/94.7

(Continued)

FOREIGN PATENT DOCUMENTS

JP  49-86478  8/1974

(Continued)

OTHER PUBLICATIONS

JP 56-34709 (abstract in English).*

*Primary Examiner*—David W. Wu
*Assistant Examiner*—Rip A. Lee
(74) *Attorney, Agent, or Firm*—Oblon, Spivak, McClelland, Maier & Neustadt, P.C.

(57) ABSTRACT

There is disclosed a process for producing an α-olefin oligomer by subjecting an α-olefin to oligomerization reaction in the presence of a catalyst and an organic solvent which comprises the step of spraying a solvent containing the organic solvent in the form of a linear or bar-like pressure fluid toward a wall surface of a vapor phase portion of a reactor from a nozzle fitted within a space of the vapor phase portion of the reactor to conduct the oligomerization reaction while cleaning the wall surface of the vapor phase portion of the reactor. In the production process of the present invention, it is possible to effectively prevent deposition of polymers onto the wall surface of the vapor phase portion of the reactor and stably operate the reactor for a long period of time.

2 Claims, 4 Drawing Sheets

U.S. PATENT DOCUMENTS

| | | | |
|---|---|---|---|
| 3,842,055 A * | 10/1974 | Gabriel et al. | 526/74 |
| 4,038,473 A * | 7/1977 | Cohen | 526/62 |
| 5,115,052 A * | 5/1992 | Wamura et al. | 526/87 |
| 5,523,508 A * | 6/1996 | Krawczyk et al. | 585/523 |
| 6,209,552 B1 * | 4/2001 | Dobbelaar et al. | 134/22.18 |
| 6,214,943 B1 | 4/2001 | Newton et al. | 526/68 |
| 6,576,721 B2 | 6/2003 | Kobayashi et al. | 526/70 |
| 6,722,377 B1 * | 4/2004 | Bruce et al. | 134/22.17 |

FOREIGN PATENT DOCUMENTS

| | | | |
|---|---|---|---|
| JP | 56-34709 | * | 4/1981 |
| JP | 7-157444 | | 6/1995 |
| JP | 9-77806 | * | 3/1997 |
| JP | 9-194400 | | 7/1997 |
| WO | 91/2707 | | 3/1991 |
| WO | WO 91/02707 A1 | * | 3/1991 |

* cited by examiner

PROCESS FOR PRODUCING LOW POLYMER OF α-OLEFIN

TECHNICAL FIELD

The present invention relates to a process for producing α-olefin oligomers. More particularly, the present invention relates to a process for producing α-olefin oligomers by subjecting α-olefins to oligomerization reaction in the presence of a catalyst and an organic solvent, in which polymers can be effectively prevented from being deposited onto a wall surface of a vapor phase portion of a reactor to thereby allow the reactor to be stably operated for a long period of time.

BACKGROUND ARTS

Alpha-olefin oligomers having unsaturated double bonds and about 4 to about 24 carbon atoms are useful substances, and have been extensively used as monomers for olefin-based polymers and comonomers for various high-molecular polymers as well as raw materials for plasticizers, surfactants or the like. The α-olefin oligomers have been generally produced by oligomerizing ethylene in a solvent in the presence of a Ziegler catalyst.

However, in the oligomerization reaction, there is such a tendency that high-molecular polymers by-produced are deposited onto a wall surface of a vapor phase portion located in an upper part of a reactor with the passage of time. If the oligomerization reaction is continued without removal of the high-molecular polymers deposited, gradual growth of the polymers occurs, and the grown polymers are finally dropped in a reaction solution owing to increase in their weight. The high-molecular polymers dropped and included in the reaction solution will cause clogging of an external circulating-type heat exchanger provided for removing the heat of reaction, failure of pump or the like. Once such disadvantages occur, it is required to stop the continuous operation of the reactor and conduct time-consuming removal of the polymers deposited therein.

In order to inhibit the deposition of polymers onto the wall surface of the vapor phase portion of the reactor during polymerization reactions, for example, upon production of acrylonitrile-styrene copolymer resins, styrene resins or polymethyl methacrylate, there is known the method in which a mixed solution of monomers as raw materials and a solvent is sprayed into an upper vapor phase space of the reactor to wet the wall surface of the vapor phase portion of the reactor and thereby reduce the amount of the polymers deposited thereonto (Japanese Patent Application Laid-open No. 9-77806). However, this publication fails to mention details of the spraying method, though it is only described that the solution to be sprayed is kept at a temperature of 0 to 60° C.

Also, there is known the technique in which a part of a solvent is atomized and supplied to a vapor phase portion of a reactor to increase a concentration of the solvent in the vapor phase portion for preventing the deposition of scales thereon (Japanese Patent Application Laid-open No. 49-86478). However, this technique is applicable only to limited polymers such as polyacrylonitrile.

SUMMARY OF THE INVENTION

The present invention has been made in view of the above problems. An object of the present invention is to provide a process for producing α-olefin oligomers by subjecting α-olefins to oligomerization reaction in the presence of a catalyst and an organic solvent, in which polymers can be effectively prevented from being deposited onto a wall surface of a vapor phase portion of a reactor to thereby allow the reactor to be stably operated for a long period of time.

As a result of extensive researches, the present inventors have found that the above object is achieved by spraying the same solvent as used in the oligomerization reaction in the form of a linear or bar-like pressure fluid toward a wall surface of a vapor phase portion of a reactor from a nozzle fitted within a space of the vapor phase portion of the reactor. The present invention has been accomplished on the basis of this finding.

Thus, the present invention provides a process for producing an α-olefin oligomer by subjecting an α-olefin to oligomerization reaction in the presence of a catalyst and an organic solvent, comprising the step of spraying a solvent containing the organic solvent in the form of a linear or bar-like pressure fluid toward a wall surface of a vapor phase portion of a reactor from a nozzle fitted within a space of the vapor phase portion of the reactor to conduct the oligomerization reaction while cleaning the wall surface of the vapor phase portion of the reactor.

PREFERRED EMBODIMENT TO CARRY OUT THE INVENTION

Figure 1:
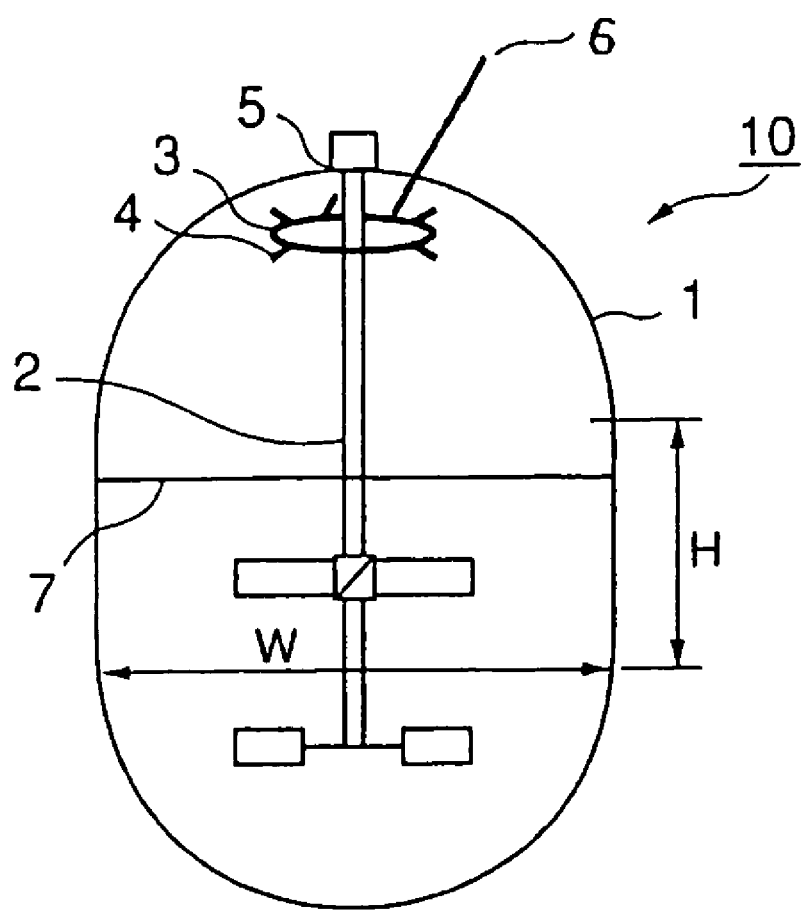
FIG. 1 is a schematic view showing an example of a reactor used in the process for producing α-olefin oligomers according to the present invention.

In the process for producing α-olefin oligomers according to the present invention, α-olefins as raw materials are subjected to oligomerization reaction in the presence of a catalyst and an organic solvent.

The α-olefins used as raw materials in the oligomerization reaction are not restricted to particular ones, and include, for example, $C_2$-$C_4$ α-olefins such as ethylene and propylene. Of these α-olefins, ethylene is especially preferred.

As the catalyst, there may be used Ziegler catalysts and chromium-based catalysts. In general, Ziegler catalysts are suitably used.

More specifically, as the suitable Ziegler catalysts, there may be used catalyst systems comprising the combination of (A) a transition metal compound, (B) an organoaluminum compound, and (C) an optional third component used if required.

As the transition metal compound (A), there may be used those compounds represented by the general formula (I):

$$MX_xY_yO_z \qquad (I)$$

wherein M is a zirconium atom or a titanium atom; X is a halogen atom selected from chlorine, bromine and iodine; and Y is RO—, $R_2N$—, —OCOR, —$OSO_3R$, R—, -Cp (cyclopentadienyl) wherein R is linear or branched $C_1$ to $C_{20}$ alkyl, or a β-diketonato group represented by the general formula (II):

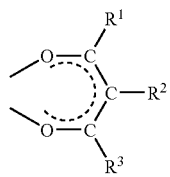

(II)

wherein $R^1$, $R^2$ and $R^3$ are independently a hydrogen atom, $C_1$ to $C_{20}$ alkyl or $C_1$ to $C_{20}$ halogen-substituted alkyl with the proviso that one of $R^1$, $R^2$ and $R^3$ is $C_1$ to $C_{20}$ halogen-substituted alkyl; and x, y and z are respectively an integer of 0 to 4 with the proviso that (x+y+z) is 4.

Specific examples of the transition metal compound include $ZrCl_4$, $ZrBr_4$, $ZrI_4$, $ZrBrCl_3$, $ZrBr_2Cl_2$, $TiCl_4$, $TiBr_4$, $TiI_4$, $TiBrCl_3$, $TiBr_2Cl_2$, $Zr(OC_2H_5)_4$, $Zr(OC_2H_5)_2Cl_2$, $Zr(O$-$n$-$C_3H_7)_4$, $Zr(O$-$n$-$C_3H_7)_2Cl_2$, $Zr(O$-$iso$-$C_3H_7)_4$, $Zr(O$-$iso$-$C_3H_7)_2Cl_2$, $Zr(O$-$n$-$C_4H_9)_4$, $Zr(O$-$n$-$C_4H_9)_2Cl_2$, $Zr(O$-$iso$-$C_4H_9)_4$, $Zr(O$-$iso$-$C_4H_9)_2Cl_2$, $Zr(O$-$tert$-$C_4H_9)_4$, $Zr(O$-$tert$-$C_4H_9)_2Cl_2$, $Zr((CH_3)_2N)_4$, $Zr((C_2H_5)_2N)_4$, $Zr((n$-$C_3H_7)_2N)_4$, $Zr((iso$-$C_3H_7)_2N)_4$, $Zr((n$-$C_4H_9)_2N)_4$, $Zr((tert$-$C_4H_9)_2N)_4$, $Zr(OSO_3CH_3)_4$, $Zr(OSO_3C_2H_5)_4$, $Zr(OSO_3C_3H_7)_4$, $Zr(OSO_3C_4H_9)_4$, $ZrCp_2Cl_2$, $ZrCp_2ClBr$, $Ti(OC_2H_5)_4$, $Ti(OC_2H_5)_2Cl_2$, $Ti(O$-$n$-$C_3H_7)_4$, $Ti(O$-$n$-$C_3H_7)_2Cl_2$, $Ti(O$-$iso$-$C_3H_7)_4$, $Ti(O$-$iso$-$C_3H_7)_2Cl_2$, $Ti(O$-$n$-$C_4H_9)_4$, $Ti(O$-$n$-$C_4H_9)_2Cl_2$, $Ti(O$-$iso$-$C_4H_9)_4$, $Ti(O$-$iso$-$C_4H_9)_2Cl_2$, $Ti(O$-$tert$-$C_4H_9)_4$, $Ti(O$-$tert$-$C_4H_9)_2Cl_2$, $Ti((CH_3)_2N)_4$, $Ti((C_2H_5)_2N)_4$, $Ti((n$-$C_3H_7)_2N)_4$, $Ti((iso$-$C_3H_7)_2N)_4$, $Ti((n$-$C_4H_9)_2N)_4$, $Ti((tert$-$C_4H_9)_2N)_4$, $Ti(OSO_3CH_3)_4$, $Ti(OSO_3C_2H_5)_4$, $Ti(OSO_3C_3H_7)_4$, $Ti(OSO_3C_4H_9)_4$, $TiCp_2Cl_2$, $TiCp_2ClBr$, $Zr(OCOC_2H_5)_4$, $Zr(OCOC_2H_5)_2Cl_2$, $Zr(OCOC_3H_7)_4$, $Zr(OCOC_3H_7)_2Cl_2$, $Zr(OCOC_4H_9)_4$, $Zr(OCOC_4H_9)_2Cl_2$, $Ti(OCOC_2H_5)_4$, $Ti(OCOC_2H_5)_2Cl_2$, $Ti(OCOC_3H_7)_4$, $Ti(OCOC_3H_7)_2Cl_2$, $Ti(OCOC_4H_9)_4$, $Ti(OCOC_4H_9)_2Cl_2$, $ZrCl_2(HCOCFCOF)_2$, $ZrCl_2(CH_3COCFCOCH_3)_2$ or the like. These transition metal compounds (A) may be used alone or in combination of any two or more thereof.

As the organoaluminum compound (B), there may be used those compounds represented by the general formula (III):

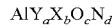

(III)

wherein X is a halogen atom selected from chlorine, bromine and iodine; Y is RO—, $R_2N$—, —OCOR or R— wherein R is linear or branched $C_1$, to $C_{20}$ alkyl; and a, b, c and d are respectively an integer of 0 to 3 with the proviso that (a+b+c+d) is equal to 3, and/or those compounds represented by the general formula (IV):

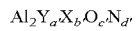

(IV)

wherein X is a halogen atom selected from chlorine, bromine and iodine; Y is RO—, $R_2N$—, —OCOR, —RCOCR'COR" or R— wherein R, R' and R" are respectively linear or branched $C_1$ to $C_{20}$ alkyl; and a', b', c' and d' are respectively an integer of 0 to 6 with the proviso that (a'+b'+c'+d') is equal to 6.

Examples of the organoaluminum compound represented by the above general formula (III) include $Al(CH_3)_3$, $Al(C_2H_5)_3$, $Al(C_3H_7)_3$, $Al(iso$-$C_3H_7)_3$, $Al(C_4H_9)_3$, $Al(iso$-$C_4H_9)_3$, $Al(C_5H_{11})_3$, $Al(C_6H_{13})_3$, $Al(C_8H_{17})_3$, $Al(C_2H_5)_2Cl$, $Al(C_2H_5)_2Br$, $Al(C_2H_5)_2I$, $Al(C_2H_5)Cl_2$, $Al(C_2H_5)Br_2$, $Al(C_2H_5)I_2$, $AlC_2H_5(OC_2H_5)_2$, $AlC_2H_5(OC_3H_7)_2$, $AlC_2H_5(OC_4H_9)_2$, $Al(OC_2H_5)_2Cl$, $Al(OC_3H_7)_2Cl$, $Al(OC_4H_9)_2Cl$, $Al(OC_2H_5)Cl_2$, $Al(OC_3H_7)Cl_2$, $Al(OC_4H_9)Cl_2$, $AlC_2H_5(OCOC_2H_5)_2$, $AlC_2H_5(OCOC_3H_7)_2$, $AlC_2H_5(OCOC_4H_9)_2$, $Al(OCOC_2H_5)_2Cl$, $Al(OCOC_3H_7)_2Cl$, $Al(OCOC_4H_9)_2Cl$, $Al(OCOC_2H_5)Cl_2$, $Al(OCOC_3H_7)Cl_2$, $Al(OCOC_4H_9)Cl_2$, $Al(C_2H_5)_2OC_2H_5$, $Al(C_2H_5)_2OC_3H_7$, $Al(C_2H_5)_2OC_4H_9$, $Al(C_2H_5)_2N(C_2H_5)_2$, $Al(C_2H_5)_2N(C_3H_7)_2$, $Al(C_2H_5)_2N(C_4H_9)_2$ or the like.

Examples of the organoaluminum compound represented by the above general formula (IV) include $Al_2(CH_3)_3Cl_3$, $Al_2(CH_3)_3Br_3$, $Al_2(C_2H_5)_3Cl_3$, $Al_2(C_2H_5)_3Br_3$, $Al_2(C_2H_5)_3I_3$, $Al_2(C_2H_5)_3BrCl_2$, $Al_2(C_3H_7)_3Cl_3$, $Al_2(iso$-$C_3H_7)_3Cl_3$, $Al_2(C_4H_9)_3Cl_3$, $Al_2(iso$-$C_4H_9)_3Cl_3$, $Al_2(C_5H_{11})_3Cl_3$, $Al_2(C_8H_{17})_3Cl_3$, $Al_2(C_2H_5)_2(CH_3)Cl_3$, $Al_2(OC_2H_5)_3Cl_3$, $Al_2(OC_3H_7)_3Cl_3$, $Al_2(OC_4H_9)_3Cl_3$, $Al_2(OCOC_2H_5)_3Cl_3$, $Al_2(OCOC_3H_7)_3Cl_3$, $Al_2(OCOC_4H_9)_3Cl_3$ or the like.

These organoaluminum compounds (B) may be used alone or in combination of any two or more thereof.

Further, as the optional third component (C) that may be used according to requirements, there may be used at least one compound selected from the group consisting of sulfur compounds, phosphorus compounds and nitrogen compounds. The third component (C) contributes to improvement in purity of the α-olefin oligomers as aimed products.

The sulfur compounds usable in the present invention are not particularly restricted as long as they are organosulfur compounds. Examples of the sulfur compounds include thioethers such as dimethyl sulfide, diethyl sulfide, dipropyl sulfide, dihexyl sulfide, dicyclohexyl sulfide and diphenyl thioether; dialkyl disulfide compounds such as dimethyl disulfide, diethyl disulfide, dipropyl disulfide, dibutyl disulfide, dihexyl disulfide, dicyclohexyl disulfide and ethylmethyl disulfide; thiophenes such as thiophene, 2-methyl thiophene, 3-methyl thiophene, 2,3-dimethyl thiophene, 2-ethyl thiophene and benzothiophene; heterocyclic sulfur compounds such as tetrahydrothiophene and thiopyran; aromatic sulfur compounds such as diphenyl sulfide, diphenyl disulfide, methylphenyl disulfide and methylphenyl sulfide; thiourea; sulfides such as methyl sulfide, ethyl sulfide and butyl sulfide; or the like.

The phosphorus compounds usable in the present invention are not particularly restricted as long as they are organophosphorus compounds. Examples of the suitable phosphorus compounds include phosphines such as triphenyl phosphine, triethyl phosphine, tributyl phosphine, tripropyl phosphine, trioctyl phosphine and tricyclohexyl phosphine.

The nitrogen compounds usable in the present invention are not particularly restricted as long as they are organonitrogen compounds. Examples of the suitable nitrogen compounds include organic amines such as methyl amine, ethyl amine, propyl amine, butyl amine, pentyl amine, hexyl amine, cyclohexyl amine, octyl amine, decyl amine, aniline, benzyl amine, naphthyl amine, dimethyl amine, diethyl amine, dibutyl amine, diphenyl amine, methylphenyl amine, trimethyl amine, triethyl amine, tributyl amine, triphenyl amine, pyridine and picoline.

In the present invention, of various sulfur compounds, phosphorus compounds and nitrogen compounds as mentioned above, for example, at least one compound selected from the group consisting of dimethyl disulfide, thiophene, thiourea, triphenyl phosphine, tributyl phosphine, trioctyl phosphine, aniline and the like, is especially preferably used as the component (C).

Examples of the organic solvent used in the oligomerization reaction according to the present invention include naphthene-based hydrocarbons such as cyclohexane and decaline; aromatic hydrocarbons such as benzene, toluene, xylene, chlorobenzene, ethyl benzene, dichlorobenzene and chlorotoluene, or halogen-substituted compounds thereof; aliphatic hydrocarbons such as pentane, hexane, heptane, octane, nonane and decane; haloalkanes such as dichloroethane and dichlorobutane; or the like. Of these organic solvents, preferred are hydrocarbon-based solvents. These organic solvents may be used alone or in the form of a mixture of any two or more thereof.

The respective mixing ratios of the components (A), (B) and (C) relative to the organic solvent are as follows. That is, the component (A) may be used in an amounts of usually 0.01 to 5 mmol, preferably 0.03 to 1 mmol per 250 ml of the organic solvent; the component (B) may be used in an amount of usually 0.05 to 15 mmol, preferably 0.06 to 3 mmol per 250 ml of the organic solvent; and the component (C) may be used in an amount of usually 0.05 to 20 mmol, and preferably 0.1 to 10 mmol when the sulfur compounds are used as the component (C), or 0.05 to 5 mmol when the nitrogen compounds or the phosphorus compounds are used as the component (C), per 250 ml of the organic solvent.

Also, the mixing ratios of the components (A) and (B) are more preferably controlled such that the molar ratio of Al/Zr or Al/Ti is in the range of 1 to 15.

The oligomerization reaction of the present invention may be usually performed at a temperature of 115 to 160° C. under a pressure of 2.94 to 8.82 MPa-G. The reaction time varies depending upon the temperature and pressure and, therefore, cannot be limited to a specific range. However, the residence time in the reactor is usually about 10 to about 60 minutes.

The α-olefin oligomers obtained by the production process of the present invention are various oligomers having 4 or more carbon atoms, especially 4 to 18 carbon atoms. Specific examples of the α-olefin oligomers include ethylene oligomers such as 1-butene, 1-hexene, 1-octene, 1-decene, 1-dodecene, 1-tetradecene, 1-hexadecene, 1-octadecene or the like. The α-olefin oligomers produced according to the present invention may be in the from of a mixture of any two or more of these ethylene oligomers.

In the process for producing the α-olefin oligomers according to the present invention, a solvent containing the same solvent as used in the oligomerization reaction is sprayed in the form of a linear or bar-like pressure fluid toward a wall surface of a vapor phase portion of the reactor and, if required, toward a mechanical seal or a rotating shaft of a stirrer from a nozzle fitted within a space of the vapor phase portion of the reactor to conduct the oligomerization reaction of α-olefins while cleaning the wall surface of the vapor phase portion of the reactor. It is more preferable to spray the solvent in the form of a bar-like pressure fluid. The bar-like pressure fluid means that the solvent is straightly sprayed without scattering around. When the solvent is sprayed in the form of such a bar-like pressure fluid, the sprayed solvent can surely reach the intended positions. The solvent containing the same organic solvent as used in the oligomerization reaction may also contain various other solvents in addition to the organic solvent unless the oligomerization reaction and the objects of the present invention are adversely affected by the use of such solvents.

In FIG. 1, there is schematically shown an example of the reactor used in the process for producing the α-olefin oligomers according to the present invention. As shown in FIG. 1, a ring 3 having a plurality of bar-shaped nozzles 4 is fitted to a vapor phase portion of a reactor 10 equipped with a stirrer 2. The bar-shaped nozzles 4 have such a structure capable of spraying the solvent in the form of a bar-like pressure fluid toward the wall surface 1 of the vapor phase portion of the reactor or a mechanical seal 5. Reference numerals 6 and 7 represent an inlet pipe for the solvent to be sprayed, and a liquid level of a reaction solution, respectively.

In the present invention, a distance between a tip end of each nozzle and the portion to which the solvent should be sprayed is preferably 20 cm or shorter in order to allow the sprayed solvent to surely reach the wall surface or the mechanical seal. The reaction pressure is usually as high as about 2.94 to about 8.82 MPa.G, so that the vapor density of the vapor phase portion is extremely high. Therefore, if the solvent sprayed is not in the form of a bar-like pressure fluid and the distance between the tip end of each nozzle and the position to which the solvent should be sprayed is more than 20 cm, there may occur such a risk that the sprayed solvent fails to reach the aimed position.

Further, the sprayed solvent preferably has a temperature of 110° C. or higher from the standpoint of good cleaning effect, and the pressure fluid sprayed from each nozzle preferably has a pressure higher by about 0.3 to 1.0 MPa than the pressure within the reactor. If the difference between the pressure of the sprayed solvent and that within the reactor is less than 0.3 MPa, there may occur such a disadvantage that the sprayed solvent cannot be reach the desired positions, thereby failing to attain a sufficient cleaning effect. On the other hand, even though the pressure difference is more than 1.0 MPa, the cleaning effect cannot be enhanced to such an extent corresponding to the large pressure difference.

Moreover, in the case of the reactor whose vapor phase portion has an elongated length in a vertical direction thereof, the cleaning effect for a lower wall surface of the vapor phase portion can be enhanced, for example, by providing a plurality of rings each having the same structure as shown in FIG. 1 in a multi-stage manner.

The present invention will be described in more detail with reference to the following examples, but these examples are not intended to limit the present invention thereto.

Figure 2:
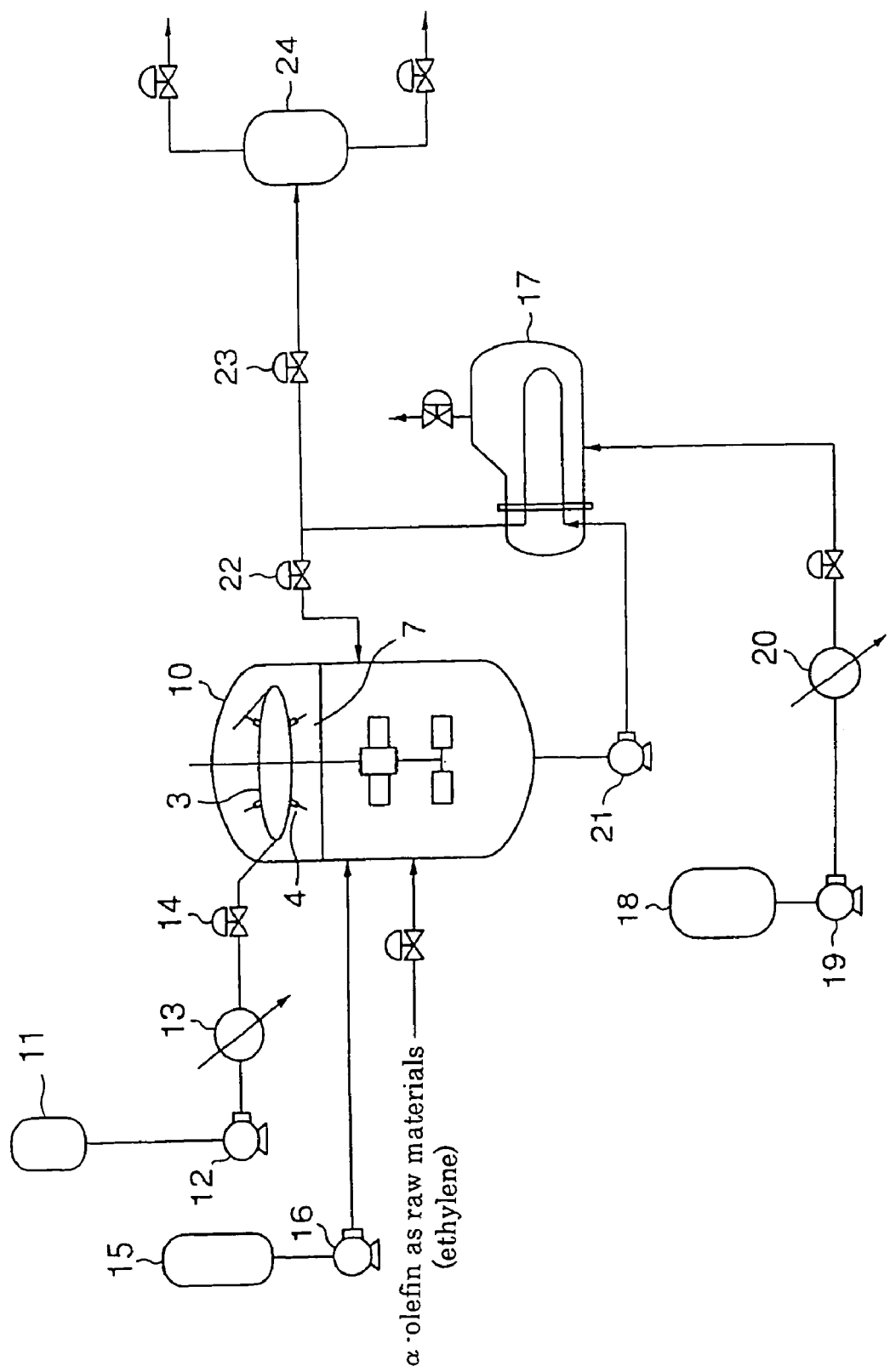
FIG. 2 is a schematic view of a reaction apparatus used in Examples and Comparative Examples.

Meanwhile, the following examples and comparative examples have been performed using the reaction apparatus schematically shown in FIG. 2.

EXAMPLE 1

(1) Preparation of Catalyst

A 5-liter pot equipped with a stirrer was charged with 250 mmol of anhydrous zirconium tetrachloride and 2.5 l of dried cyclohexane in an argon atmosphere, and the contents of the pot were stirred at room temperature for 10 minutes. The resultant mixture was mixed with triethyl aluminum [$(C_2H_5)_3Al$] and then with ethyl aluminum sesquichloride [$(C_2H_5)_3Al_2Cl_3$]. The triethyl aluminum and ethyl aluminum sesquichloride were used in such amounts that the molar ratio of $(C_2H_5)_3Al/(C_2H_5)_3Al_2Cl_3$ was 3.5, and the molar ratio of $[(C_2H_5)_3Al_2Cl_3+(C_2H_5)_3Al]/ZrCl_4$ was 7.

After completion of adding all the components, the resultant mixture was stirred under heating at 70° C. for 2 hours in an argon atmosphere to form a complex and prepare a catalyst solution. The thus prepared catalyst solution was diluted with dried cyclohexane up to 100 times by volume, and charged into a catalyst tank 15.

(2) Oligomerization of Ethylene

The oligomerization reaction was continuously conducted using the reactor 10 of a complete mixing vessel type equipped with an external circulating loop for heat removal (height (H): 0.3 m; width (W): 0.6 m; inner capacity: about 200 liters) as schematically shown in FIG. 1.

Cyclohexane as a solvent was fed from a solvent tank 11 through a pump 12 to the reactor 10 at a flow rate of 500 liters/hr. The flow rate of the cyclohexane solvent was controlled at a valve 14.

Figure 3:
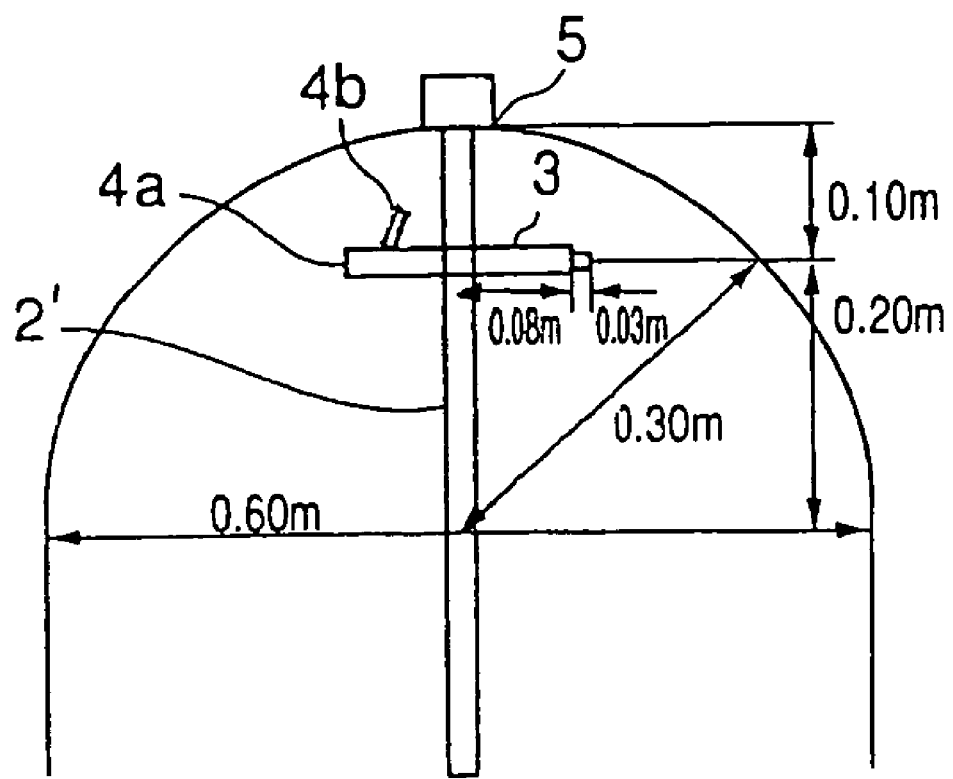
FIG. 3 is a side view of the reactor used in Examples which shows a position of a nozzle fitted therein.
Figure 4:
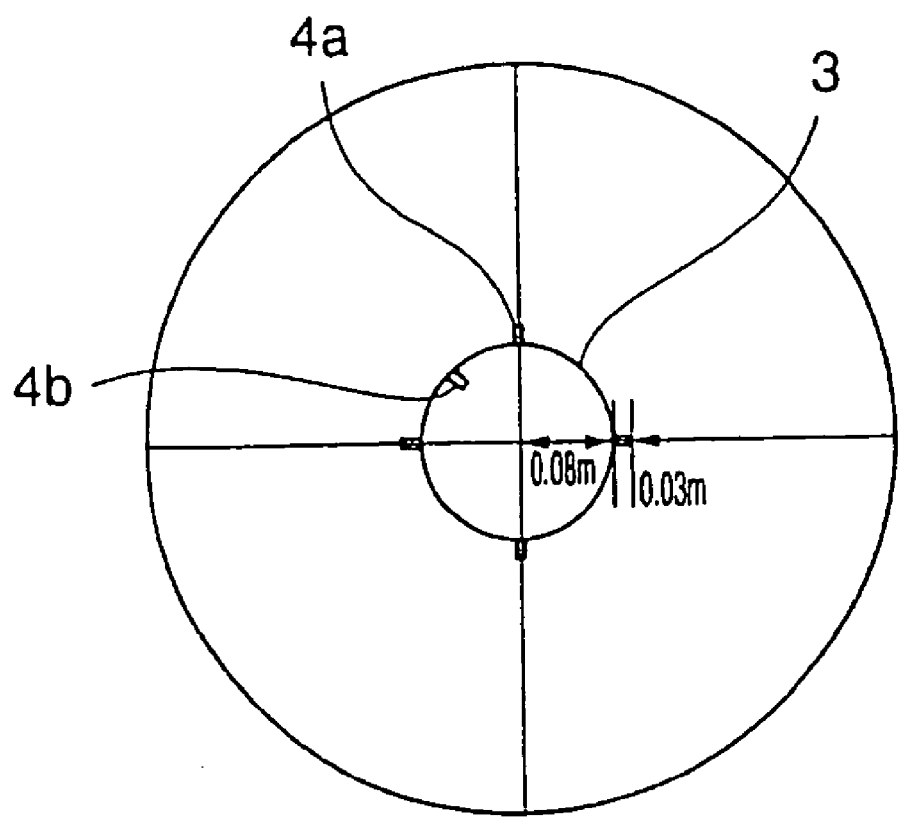
FIG. 4 is a top plan view of the reactor used in Examples which shows a position of a nozzle fitted therein.

The cyclohexane solvent was heated to 135° C. by a heater 13, and then sprayed from nozzles 4 fitted to a ring 3. The nozzles 4 were constituted from four nozzles 4a directed toward a wall surface of the reactor, and one nozzle 4b directed toward a mechanical seal. The fitting positions of these nozzles 4 are shown in FIGS. 1, 3 and 4. FIG. 3 is a side view showing the fitting positions of the nozzles; and FIG. 4 is a top plan view showing the fitting positions of the nozzles. In addition, the nozzles 4 was of such a type capable of spraying the solvent in the form of a bar-like pressure fluid (i.e., straight jet without scattering around). The distance between the tip end of each nozzle and the position to which the solvent was to be sprayed, was set to 11 cm, and the pressure difference at the nozzles was about 0.5 MPa. Meanwhile, in FIG. 3, reference numeral 2' represents a rotating shaft of a stirrer.

The catalyst solution diluted with cyclohexane was fed from a catalyst tank 15 through a pump 16 to the reactor 10 at a flow rate of 40 liters/hr. The solvent tank 11 and the catalyst tank 15 were appropriately replenished with cyclohexane and the catalyst solution, respectively, when the liquid levels of these tanks were lowered to predetermined heights.

A high-purity ethylene gas was continuously supplied to a liquid phase side of the reactor so as to maintain the reaction pressure at 6.4 MPa-G.

While controlling the liquid level of the reactor 10 by a valve 23 so as to keep the volume of the reaction solution therein constant at 120 liters, the reaction solution was fed to a flasher 24. The residence time at the reactor 10 was controlled to about 13 minutes on the basis of the solvent (cyclohexane). The contents of the reactor 10 was stirred by two-stage stirring blades at a rotational speed of 200 rpm. Slant paddle blades were used as the upper stage stirring blades, and turbine blades were used as the lower stage stirring blades.

The heat of reaction was removed by circulating the reaction solution through a shell-and-tube type heat exchanger 17 fitted to the external circulating loop (heat transfer area: 10 m$^2$) by a pump 21. The heat exchanger 17 was supplied with water under pressure from a water tank 18 through a pump 19 and a heater 20 where the water was heated to 100° C. The water supplied to the heat exchanger was evaporated into steam for removing the heat from the reaction solution circulated therethrough so as to keep the temperature within the reactor 10 constant at 130° C. The flow rate of the reaction solution circulated was controlled by a valve 22 such that the temperature of the reaction solution at an outlet of the heat exchanger 17 was kept constant at 125° C.

After being continuously operated for 720 hours, the reactor 10 was opened to examine whether or not any polymer scales were deposited on the vapor phase portion thereof As a result, it was confirmed that no polymers were deposited on the vapor phase portion.

EXAMPLE 2

The oligomerization of ethylene was performed in the same manner as in EXAMPLE 1 except for setting the solvent temperature at an outlet of the heater 13 at 120° C.

After being continuously operated for 720 hours, the reactor 10 was opened to examine whether or not any polymer scales were deposited on the vapor phase portion thereof. As a result, it was confirmed that no polymers were deposited on the vapor phase portion.

EXAMPLE 3

The oligomerization of ethylene was performed in the same manner as in EXAMPLE 1 except for setting the solvent temperature at an outlet of the heater 13 at 100° C.

After being continuously operated for 720 hours, the reactor 10 was opened to examine whether or not any polymer scales were deposited on the vapor phase portion thereof As a result, it was confirmed that the polymers were deposited in the form of a thin film on a lower part of the vapor phase portion of the reactor.

COMPARATIVE EXAMPLE 1

The oligomerization of ethylene was performed in the same manner as in EXAMPLE 1 except for using full cone nozzles for spraying the solvent in a conically and circularly spread manner instead of the bar-shaped nozzles 4.

After being continuously operated for 720 hours, the reactor 10 was opened to examine whether or not any polymer scales were deposited on the vapor phase portion thereof As a result, it was confirmed that the polymers with a thickness of about 5 mm were deposited on a substantially entire surface of the vapor phase portion of the reactor.

INDUSTRIAL APPLICABILITY

In accordance with the process of the present invention, when producing α-olefin oligomers by subjecting α-olefins to oligomerization reaction in the presence of a catalyst and an organic solvent, it is possible to effectively prevent polymers from being deposited on a wall surface of a vapor phase portion of a reactor, so that the reactor can be stably operated for a long period of time.

The invention claimed is:

1. A process for producing an α-olefin oligomer by subjecting ethylene to an oligomerization reaction in a reactor in the presence of a Ziegler catalyst and a hydrocarbon-based solvent, comprising the step of spraying the hydrocarbon-based solvent in the form of a linear or bar-shaped pressure fluid, at a pressure 0.3 to 1.0 MPa higher than the pressure within the reactor, toward a wall surface of a vapor phase portion of the reactor from a nozzle fitted within a space of the vapor phase portion of the reactor to conduct the oligomerization reaction while cleaning the wall surface of the vapor phase portion of the reactor, keeping a distance between the nozzle and the wall surface of no more than 20 cm, wherein the linear or bar-shaped pressure fluid consists of the hydrocarbon-based solvent.

2. The process according to claim 1, wherein the pressure fluid sprayed has a temperature of 110° C. or higher.

* * * * *